United States Patent [19]

Grabley et al.

[11] Patent Number: 5,100,588
[45] Date of Patent: Mar. 31, 1992

[54] PROCESS FOR THE PREPARATION OF ACYLOXYBENZENESULFONIC ACIDS AND THEIR SALTS

[75] Inventors: Fritz-Feo Grabley, Köigstein/Taunus; Gerd Reinhardt, Kelkheim; Roland Steinl, Hattersheim am Main, all of Fed. Rep. of Germany

[73] Assignee: Hoechst Aktiengesellschaft, Frankfurt am Main, Fed. Rep. of Germany

[21] Appl. No.: 154,057

[22] Filed: Feb. 9, 1988

Related U.S. Application Data

[63] Continuation of Ser. No. 881,226, Jul. 2, 1986, abandoned.

[30] Foreign Application Priority Data

Jul. 5, 1985 [DE] Fed. Rep. of Germany ....... 3524052

[51] Int. Cl.$^5$ .................. C07C 309/58; C07C 303/06; C07C 303/32
[52] U.S. Cl. ..................................... 260/402; 560/142
[58] Field of Search .................... 560/142; 260/512 R, 260/402

[56] References Cited

U.S. PATENT DOCUMENTS 3,320,292  5/1967  Cahn et al. .
3,394,155  7/1968  Cahn et al. .
3,503,888  3/1970  Miller et al. .

FOREIGN PATENT DOCUMENTS 0098129  1/1984  European Pat. Off. .
0105672  4/1984  European Pat. Off. .
0105673  4/1984  European Pat. Off. .
0125641  11/1984 European Pat. Off. .
 666626  10/1938 Fed. Rep. of Germany .
 820659   9/1959 United Kingdom ............ 260/512 R

*Primary Examiner*—Vivian Garner

[57] ABSTRACT

The process for the preparation of acyloxybenzenesulfonic acids of the general formula

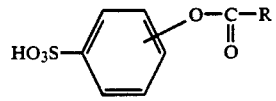

in which R denotes a $(C_1-C_{17})$-alkyl or $(C_2-C_{17})$-alkenyl radical, or alkali metal, alkaline earth metal or ammonium salts thereof, is carried out in the following stages: (a) sulfonation of phenol, (b) heat treatment of the phenolsulfonic acid formed as the intermediate product, (c) esterification of the phenolsulfonic acid and, if appropriate, (d) neutralization of the resulting $(C_2-C_{18})$-acyloxybenzenesulfonic acid. As a result of the incorporation of stage (b), the process affords products in which the proportion of the 1,4-isomer compared with the 1,2-isomer is markedly increased, as a result of which these products can be used, in particular, as perborate activators in detergents.

2 Claims, No Drawings

PROCESS FOR THE PREPARATION OF ACYLOXYBENZENESULFONIC ACIDS AND THEIR SALTS

CROSS REFERENCE TO RELATED APPLICATIONS

This is a continuation of our copending application Ser. No. 881,226, filed July 2, 1986, now abandoned.

The invention relates to a process for the preparation of acyloxybenzenesulfonic acids and their salts in a multi-stage reaction sequence, starting from phenol.

Acyloxybenzenesulfonic acids and their salts are compounds having a surfactant action which have been known for a long time and for which there are several possible means of preparation.

A process in which esters formed from phenols and saturated alkanemonocarboxylic acids having at least 10 carbon atoms are reacted with a sulfonating agent, such as chlorosulfonic acid, oleum or $SO_3$, and the reaction product is subsequently neutralized, is described as early as in DE-C 666,626. A small amount of phosphorus chloride or oxychloride or thionylchloride is added during, before or after the sulfonation. The reaction products are stated to be capable of use, for example, as detergents.

A process is disclosed in U.S. Pat. No. 3,320,292 in which hydroxyalkanesulfonates or hydroxybenzenesulfonates are esterified directly with organic $(C_8-C_{20})$-alkanoic acids at 200° to 240° C. in the presence of zinc oxide or organic zinc salts; however, no aromatic sulfonates are employed in the examples. The reaction products are stated to exhibit a surfactant action, for example as a component of soaps. In accordance with U.S. Pat. No. 3,394,155, this esterification is carried out in two stages in the presence of esterification auxiliaries such as tin sulfate, chloroacetic acid or the zinc compounds mentioned above.

In accordance with the information in U.S. Pat. No. 3,503,888, the process is carried out (a) by first sulfonating phenol with $SO_3$ in an inert organic solvent, (b) esterifying the sulfonated phenol with a fatty acid chloride, and (c) then neutralizing the ester with NaOH to a pH of 6.5 to 9; a partial hydrolysis of the resulting ester to the extent of 20 to 50% is intended as a side reaction during the neutralization in this process. The process products are used as a component of soaps. In EP-A 0,140,251, on the other hand, this process is described without saponification of the ester, the neutralization stage (stage of forming salts of the ester) being carried out by means of alkali or alkaline earth metal hydroxides, carbonates or bicarbonates at a pH of 2.5 to 7.0.

Very recently, acyloxybenzenesulfonates have also attracted interest as perborate activators in detergents; in this regard see, for example, EP-A 0,098,129, EP-A 0,105,672, EP-A 0,105,673 and EP-A 0,125,641, the acyloxybenzenesulfonates being synthesized essentially in accordance with the following methods:

heating a mixture of trifluoroacetic anhydride, Na phenolsulfonate and a $(C_6-C_{19})$-alkanoic acid, a two-stage reaction by (a) converting the alkanoic acid into the anhydride in an excess of acetic anhydride, and (b) reacting the anhydride, after isolation, with Na phenolsulfonate, heating the alkanoyl chloride (for example nonanoyl chloride) with Na phenolsulfonate at 80° to 100° C. in an organic aprotic solvent, such as dioxane, dichloroethane or toluene, using a stream of $N_2$ to remove the byproduct HCl, transesterifying a $(C_2-C_3)$-acyloxybenzenesulfonate with an excess of $(C_6-C_{18})$-alkanoic acid and removing the byproduct $(C_2-C_3)$-alkanoic acid formed, a multi-stage "one-pot" reaction by (a) converting a $(C_6-C_{18})$-alkanoic acid into the anhydride in a $(C_2-C_3)$-alkanoic anhydride, (b) removing the $(C_2-C_3)$-alkanoic acid formed, (c) reacting the anhydride with a phenolsulfonate in the presence of a strong acid or base, and (d) isolating the $(C_6-C_{18})$-acyloxybenzenesulfonate from the reaction mixture, or reacting an alkali metal phenolsulfonate or alkaline earth metal phenolsulfonate with a phenyl $(C_2-C_{31})$-alkanoate at 200° to 350° C.

However—as the large number of process variants also shows—the known methods have disadvantages of varying importance which, in some cases, also depend on the intended end use of the process products: the steps in the reactions often take place at temperatures above 200° C., so that there is a risk of side reactions and decomposition (discoloration). Mixtures of isomers which, in the course of a subsequent reaction or in the direct use of the sulfonation products, are then less effective are frequently formed in the course of the sulfonation. Some of the variants (for example transesterification reactions) can admittedly be carried out on a laboratory scale, but result in economic problems and/or ecological problems when transferred to a production scale.

The object of the present invention is, therefore, to indicate a process which can also be carried out on a large industrial scale and which results in good yields of products which are as homogeneous as possible and which can be employed in detergents, in particular in the field of application of a perborate activator.

The invention is based on the known process for the preparation of acyloxybenzenesulfonic acids of the general formula

in which R denotes a $(C_1-C_{17})$-alkyl or $(C_2-C_{17})$-alkenyl radical, or alkali metal, alkaline earth metal or ammonium salts thereof, and uses the stages of (a) sulfonation of phenol, (c) esterification of the sulfonated phenol and, if appropriate, (d) neutralization of the ester. The process according to the invention then comprises subjecting the sulfonation intermediate product of stage (a) to heat treatment in a stage (b) before the esterification.

The individual stages of the process are, in particular, carried out as described below: in the sulfonation stage (a), phenol is reacted to give phenolsulfonic acid, the compounds substituted in the 4-position being essentially formed, as well as the compounds substituted in the 2-position; in addition, however, byproducts, such as disulfonic acids or sulfones can also be formed—to a minor extent. Suitable sulfonating agents are preferably $ClSO_3H$ or $SO_3$ (liquid or gaseous). The reaction can be carried out in the presence of aprotic organic solvents, such as halogenated hydrocarbons (for example methylene chloride), toluene or ethyl acetate; it is also, however, particularly successful in solvent-free systems, and it is then possible, for example in both variants, also to add organic acids, for example $(C_2-C_{18})$-alkanoic acids, such as $CH_3COOH$ or isononanoic acid, and/or inorganic salts, such as $Na_2SO_4$ or $Na_2H_2P_2O_7$. In general, the reaction temperature is 0° C. to 120° C. and is preferably within the range from 30° to 60° C. Suitable reaction times are 0.5 to 8 hours; the amount of sulfonation agent employed is preferably 0.8 to 1.2, in particular 0.9 to 1.1, moles per mole of phenol.

In the heat treatment stage (b) which is particularly important in accordance with the invention the sulfonation product of stage (a) is subjected to heat treatment in such a way that the proportion of phenol sulfonated in the 4-position increases relatively to the proportion of phenol sulfonated in the 2-position and hence also in absolute amount. For this purpose it is preferable first to remove the organic solvent—if employed at all in stage (a)—from the reaction mixture, and then to heat the resulting phenolsulfonic acid at a temperature of, in particular, 50° to 110° C. This stage can, however, also be carried out in the presence of suitable aprotic organic solvents and/or organic acids and/or inorganic salts. Suitable examples of the additives mentioned have already been listed in the description of stage (a), and it is assumed that the addition, in particular, of alkanoic acids and inorganic salts prevents the possible formation of sulfone from the sulfonic acids. In this heat treatment, the proportion of the 4-isomer increases (relative to the proportion of the 2-isomer) from about 2 to 3 relative to 1, with no heat treatment stage to preferably about 8 to 20 relative to 1 (depending on the conditions of the heat treatment). In general, the duration of the heat treatment is 0.5 to 10 hours.

In the subsequent acylation stage (c), the free phenolsulfonic acid is esterified, the phenolsulfonic acids of stages (a) and (b) being reacted with $(C_2-C_{18})$-alkanoyl halides (especially chlorides) or anhydrides without additives, or with the free acids or their anhydrides in the presence of dehydrating agents, such as $SOCl_2$ or $POCl_3$. This stage can be carried out in the presence of aprotic organic solvents, but a solvent-free variant is also particularly successful. In general, the reaction temperature is 0° to 110° C., preferably 20 to 80° C., and the reaction time is 0.5 to 8 hours. The amount of acylating agent employed is preferably 0.8 to 1.2, in particular 0.9 to 1.1, moles per mole of sulfonic acid; if anhydrides are employed, this amount falls to 0.4 to 0.6 mole. The dehydrating agent, which is frequently employed, is as a rule added in excess. Since the formation of foam must be expected occasionally in the esterification, it is advisable in these cases to add an antifoaming agent, for example one based on silicones. The esterification stage can be followed by an after-treatment with $SOCl_2$ or $POCl_3$. Suitable acylating agents are preferably the compounds derived from a $(C_6-C_{18})$-alkanoic acid, for example isononanoic acid (3,5,5-trimethylhexanoic acid), nonanoic acid, 2-ethylhexanoic acid, dodecanoic acid, hexadecanoic acid and octadecanoic acid. The hydrocarbon radicals of these compounds can be saturated or unsaturated and linear or branched; the carboxyl group or functional group derived therefrom can also be present as a substituent within the hydrocarbon radical, but preferably it is terminal. In practice, the alkanoic acids are frequently mixtures of compounds of varying chain length or they contain varying proportions of unsaturated compounds, but on average they should fall within the above range.

The acylation stage (c) is optionally followed—if the preparation of the salts is intended—by a neutralization stage (d) in which the sulfonic acid group is converted into the salt form. The neutralization—preferably in an aqueous medium—is carried out at controlled pH values, in order to prevent as far as possible hydrolysis of the acyloxybenzenesulfonic acids formed in stage (c); it can be carried out in the range from pH 2 to 7.5, but the range from 3 to 6 is preferred. The temperature in this stage is expediently 0° to 50° C., and the bases employed are, for example, alkali metal hydroxides, carbonates or bicarbonates, alkaline earth metal hydroxides, carbonates or bicarbonates or ammonium hydroxides, carbonates or bicarbonates.

The product obtained after the completion of stages (c) or (d) is finally dried, for example by spray drying. The process according to the invention can be carried out discontinuously, but also continuously, in equipment customary in this field of operations; compared with the state of the art it displays, in particular, the following advantages:

The reaction stages are carried out in such a way and can be matched with one another in such a way that, as a result of the comparatively low temperatures, the formation of byproducts (impurities or discoloration) is as low as possible.

As a result of the heat treatment stage which has been inserted, the ratio of 4-isomers to 2-isomers in the phenolsulfonic acids formed as an intermediate product is shifted significantly towards the 4-isomer, as a result of which the effectiveness of the end product, the acyloxybenzenesulfonic acids or, in particular, the sulfonates, as a perborate activator in detergents is increased.

The process according to the invention can be carried out advantageously from the point of view of economy and ecology on a laboratory, pilot plant and large industrial scale, since it leads to good yields of highly effective products in the preparation of which troublesome byproducts are only produced to a comparatively small extent.

In the examples which follow, parts by weight are related to parts by volume as kg are to $dm^3$; % data relate in every case to weight, unless otherwise indicated. The term D-content in the following examples is to be understood as meaning the content of detergent substance in the product, which is determined by a two-phase titration as specified by EPTON. All the products have a "color number" required in industry, i.e. they are only slightly contaminated by discoloration (byproducts).

COMPARISON EXAMPLE V1

The example describes the preparation and reaction of phenolsulfonic acid without the interposed heat treatment stage (b): 94 parts by weight of phenol are melted at a temperature of 40° to 45° C. 116.5 parts by weight of chlorosulfonic acid ($ClSO_3H$) are added dropwise, with cooling, at such a rate that the reaction temperature does not exceed 50° C.; stirring is then carried out for one hour at this temperature. 176.7 parts by weight of isononanoyl chloride are added dropwise, at a temperature of 45° to 50° C. and in the course of three hours, to the resulting phenolsulfonic acid, and the reaction mixture is stirred for a further hour; during and after the completion of this stage (c), care is taken that the HCl formed is discharged. The reaction product, which is obtained in a virtually quantitative yield, has a D-content of 81%. After neutralization at a controlled pH (pH range from 2.5 to 6) with aqueous NaOH solution at about 20° C., and after the Na salt of isononanoyloxybenzenesulfonic acid has been spray-dried, the D-content is 84% and the ratio of the 4-isomer to the 2-isomer is 2.8 to 1.

COMPARISON EXAMPLE V2

This is also carried out without the heat treatment stage (b): 94 parts by weight of phenol are dissolved in 500 parts by volume of methylene chloride, and 116.5 parts by weight of ClSO$_3$H are added dropwise, at a temperature of 25° C. and in the course of 1.5 hours, at such a rate that the reaction temperature does not exceed 30° C. The mixture is stirred for a further hour, and esterification is carried out at a temperature of 30° C., in the course of 2.5 hours, by adding 176.7 parts by weight of isononanoyl chloride. After the organic solvent has been removed by distillation, the isononanoyloxybenzenesulfonic acid is isolated in a virtually quantitative yield, and, after further processing in accordance with V1, is in the form of the Na salt and has a D-content of 84% and an isomer ratio of 3.5:1.

EXAMPLE 1

The procedure followed is that of Comparison Example V1, but a heat treatment stage in which the crude phenolsulfonic acid is heated for two hours at 80° to 83° C. is interposed before the esterification. The Na salt, which is the end product, has a D-content of 88% and an isomer ratio of 9:1.

EXAMPLE 2

The procedure followed is that of Example 1, but the heat treatment stage is carried out for 1.5 hours at 95° C. The Na salt has a D-content of 84.5% and an isomer ratio of 15.5:1.

EXAMPLE 3

The procedure followed is that of Example 1, without the neutralization stage (d), but 224 parts by weight of dodecanoyl chloride are added dropwise in stage (c). The dodecanoyloxybenzenesulfonic acid obtained as the end product in this example has a D-content of 85.3% and an isomer ratio of 8.5:1.

EXAMPLE 4

The procedure followed is that of Example 1, but the heat treatment stage (b) is carried out for 2.5 hours and, in addition, the esterification stage (c) is carried out using 166 parts by weight of isononanoic acid and a little added antifoam agent based on silicones, and 130 parts by weight of thionyl chloride (SOCl$_2$) are added dropwise at a temperature of 35° C. The Na salt has a D-content of 89% and an isomer ratio of 9.5 to 1.

COMPARISON EXAMPLE V3

122 parts by weight of ClSO$_3$H are added, at a temperature of 40° C., to 94 parts by weight of phenol in 158.5 parts by weight of isononanoic acid, and stirring is continued for a further hour at 40° C. 125 parts of SOCl$_2$ are then metered in at such a rate that the evolution of gas takes place in a controlled manner, after which stirring is continued for a further hour. The Na salt of isononanoyloxybenzenesulfonic acid obtained after further working up as described in V1 has a D-content of 85% and an isomer ratio of 3.3 to 1.

EXAMPLES 5 TO 7

The procedure followed is that of Comparison Example V3, but a heat treatment stage (b) is interposed before the esterification stage (c): two hours at a temperature of 80° C. (Example 5), four hours at 80° C. (Example 6) and one hour at 95° C. (Example 7). The D-contents and isomer ratios of the products are as follows: 87% and 5.2 to 1, 86% and 7 to 1, and 86% and 8.3 to 1, respectively.

EXAMPLE 8

The phenolsulfonic acid is prepared by the procedure of Comparison Example V1 and is subjected to heat treatment at 83° C. for three hours. The intermediate product is dissolved in 146.8 parts by weight of 2-ethylhexanoic acid and is then esterified by adding 128.5 parts by weight of thionyl chloride at 40° to 45° C., after which stirring is continued for a further hour. The Na salt of 2-ethylhexanoyloxybenzenesulfonic acid obtained after further working up as described in V1 has a D-content of 86.8% and an isomer ratio of 12 to 1.

EXAMPLE 9

94 parts by weight of phenol are dissolved in 158 parts by weight of isononanoic acid and 80 parts by weight of liquid SO$_3$ are added dropwise to the mixture at a temperature of 5° C. The mixture is subjected to heat treatment at 80° C. for six hours in stage (b). Esterification is carried out by adding 125 parts by weight of SOCl$_2$ at 40° to 45° C., stirring being continued for a further hour. The Na salt of isononanoyloxybenzenesulfonic acid obtained after further working up as described in V1 has a D-content of 85% and an isomer ratio of 8.7:1.

What is claimed is:

1. A process for the preparation of acyloxybenzenesulfonic acid of the formula

in which R denotes a (C$_1$–C$_{17}$)-alkyl or (C$_2$–C$_{17}$)-alkenyl radical, or alkali metal, alkaline earth metal or ammonium salts thereof, employing the stages (a) sulfonation of phenol, (c) esterification of the sulfonated phenol and, if preparing said salts, (d) neutralization of the ester, which comprises subjecting the sulfonation intermediate product of stage (a) to heat treatment in a stage (b) before the esterification, the resulting acyloxybenzene sulfonic acid or salt being a mixture of the 4-sulfonated and 2-sulfonated isomers, but the ratio of the 4-sulfonated isomer to the 2-sulfonated isomer is at least about 8:1, and wherein, in said process, said heat treatment in stage (b) is carried out at a temperature above 50° C., and said heat treatment increases the ratio of 4-sulfonated phenol to 2-sulfonated phenol, resulting from stage (a), from about 3:1 or less to about 8:1 or more; said process including the step of subjecting the thus-altered sulfonated phenol isomeric mixture to esterification, whereby a mixture of acyloxybenzene sulfonic acid isomers is obtained in the 4-sulfonic acid isomer:2-sulfonic acid isomer ratio of at least about 8:1.

2. The process as claimed in claim 1, wherein said heat treatment in stage (b) is carried out at a said temperature up to 110° C.

* * * * *